US00PP27617P2

(12) United States Plant Patent
Egger

(10) Patent No.: US PP27,617 P2
(45) Date of Patent: Jan. 24, 2017

(54) ***KNIPHOFIA* PLANT NAMED 'BANANA POPSICLE'**

(50) Latin Name: ***Kniphofia* spp.**
Varietal Denomination: Banana Popsicle

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 34 days.

(21) Appl. No.: 14/756,170

(22) Filed: Aug. 11, 2015

(51) Int. Cl.
*A01H 5/02* (2006.01)

(52) U.S. Cl.
USPC ..... Plt./443

(58) Field of Classification Search
USPC ..... Plt./443
See application file for complete search history.

(56) References Cited

PUBLICATIONS

Declaration of Janet N. Egger dated Aug. 5, 2015.

*Primary Examiner* — Keith Robinson
(74) *Attorney, Agent, or Firm* — Klarquist Sparkman, LLP; Sheree Lynn Rybak

(57) ABSTRACT

A new and distinct *Kniphofia* plant characterized by numerous spikes of golden yellow flowers the first year, repeat blooming from July through October in Canby, Oreg., a compact habit with multiple crowns, narrow, grassy leaves, and excellent vigor, filling a one gallon pot the first year from tissue culture.

1 Drawing Sheet

Botanical denomination: *Kniphofia* spp.
Cultivar designation: 'Banana Popsicle'.

BACKGROUND OF THE INVENTION

The present invention relates to a new and distinct *Kniphofia*, and given the cultivar name 'Banana Popsicle'. *Kniphofia* is in the family Xanthorrhoeaceae. 'Banana Popsicle' is a hybrid resulting from a planned breeding program to produce a series of compact, reblooming *Kniphofia*. The cross was made using the following proprietary, unreleased plants: *Kniphofia* 84-4, as the seed parent, and *Kniphofia* 80-3, as the pollen parent. It was selected for best habit, flower color, reblooming, and crown count from many seedlings of the cross in Canby, Oreg.

Compared to the seed parent, *Kniphofia* 84-4, the new cultivar is more free-flowering.

Compared to the pollen parent, *Kniphofia* 80-3, the new cultivar has golden yellow flowers rather than bicolor light yellow to cream.

Compared to *Kniphofia* 'Lemon Popsicle', U.S. Plant Pat. No. 24,011, the new cultivar has is somewhat shorter, with larger inflorescences, with flowers that are golden yellow rather than yellow.

SUMMARY OF THE INVENTION

The new cultivar is unique and characterized by:

1. numerous spikes of golden yellow flowers the first year,
2. repeat blooming from July through October in Canby, Oreg.,
3. compact habit with multiple crowns,
4. narrow, grassy leaves, and
5. excellent vigor, filling a one gallon pot the first year from tissue culture.

This new cultivar has been reproduced only by asexual propagation (division, tissue culture). Each of the progeny exhibits identical characteristics to the new cultivar. Asexual propagation by leaf cuttings, tissue culture, and division using standard techniques as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a planting of an 18-month-old *Kniphofia* 'Banana Popsicle' in the ground in the trial bed in July in Canby, Oreg.

DETAILED PLANT DESCRIPTION

The following is a detailed description of the new *Kniphofia* cultivar based on observations of one and a half year old specimens growing in the ground outside in full sun in mid-October in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on *The Royal Horticultural Society Colour Chart,* $5^{th}$ edition, published 2007.

Plant:

*Type*.—Rhizomatous herbaceous perennial.
*Hardiness*.—USDA Zones 6 to 9.

*Size*.—Grows to 45 cm wide and 45 cm tall from the top of the soil to the top of the foliage, grows to 65 cm tall to the top of the tallest inflorescence.
*Average number of leaves/crown*.—5.
*Average number of crowns*.—About 70.
*Form*.—Clumping.

Leaf:
*Type*.—Simple.
*Shape*.—Strap-like.
*Arrangement*.—Basal rosette.
*Blade size*.—Grows to 47 cm long and 12 mm wide.
*Margins*.—Entire.
*Apex*.—Acuminate.
*Base*.—Clasping.
*Surface texture*.—Glabrous on both surfaces.
*Venation*.—Parallel.
*Color*.—Top and bottom side Green 137A.

Inflorescence:
*Type*.—Spike-like scapose raceme.
*Number of flowers per raceme*.—About 90.
*Inflorescence*.—Grows to 24 cm long and 6 cm wide.
*Peduncle description*.—Grows to 41 cm long and 5 mm wide, glabrous, Yellow Green 146B.
*Pedicle description*.—2 mm long, glabrous, Yellow Green 146C.
*Bloom time*.—Early July through October in Canby, Oreg.
*Lastingness*.—An inflorescence lasts for 2 to 4 weeks depending on the temperatures.

Flower bud:
*Size*.—27 mm long and 5 mm wide.
*Shape*.—Cylindrical.
*Surface texture*.—Glabrous
*Color*.—Yellow 13A with tips Red 45A.

Flower:
*Type*.—Actinomorphic.
*Shape*.—Cylindrical and tubular.
*Size*.—Grows to 29 mm deep and 7 mm wide.
*Texture*.—Waxy.
*Surface texture*.—Glabrous inside and outside.
*Color*.—Inside and outside, Yellow 13B.
*Corolla description*.—6 lobed fused tepals, 29 mm long and 6 mm wide, each lobe 2 mm wide and 3 mm long, ovate to oblong, margin entire, tip notched; glabrous inside and out.
*Pistil description*.—One, 29 mm long, ovary 3.5 mm long 2 mm wide, Yellow Green 144A, style extruding, 25 mm long, stigma and style Yellow 11B.
*Stamen*.—6, 33 mm long, filaments 32 mm long, and Green Yellow 1D, anthers 1 mm long and Brown 200C, pollen none.
*Fragrance*.—None.

Fruit and seed: No capsules develop.

Pest and diseases: No known resistances to pests or diseases. No problems have been observed on this plant grown under commercial conditions in Canby, Oreg.

I claim:

1. A new and distinct *Kniphofia* plant as herein shown and described.

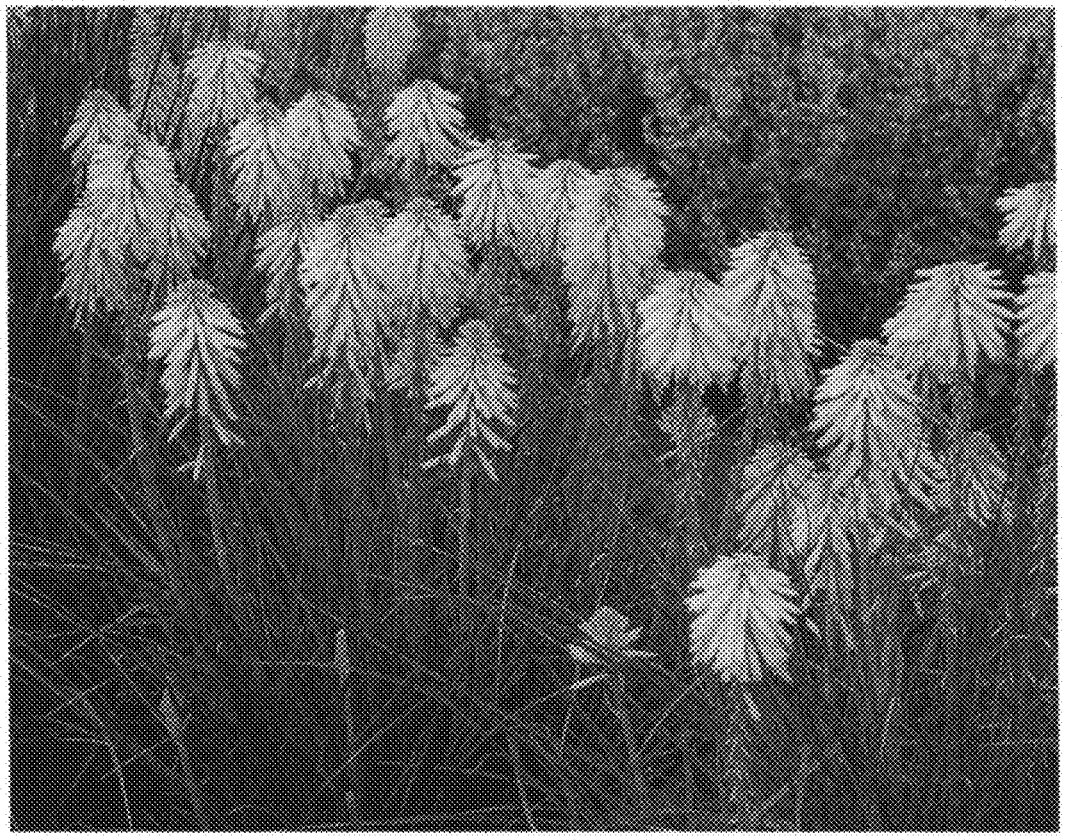

* * * * *